(12) United States Patent
Kim

(10) Patent No.: US 12,220,129 B2
(45) Date of Patent: Feb. 11, 2025

(54) ARTHROSCOPIC BLEEDING CONTROL DEVICE

(71) Applicant: Hyung Hun Kim, Seoul (KR)

(72) Inventor: Hyung Hun Kim, Seoul (KR)

(73) Assignee: Hyung Hun Kim, Seoul (KR)

(*) Notice: Subject to any disclaimer, the term of this patent is extended or adjusted under 35 U.S.C. 154(b) by 630 days.

(21) Appl. No.: 17/512,009

(22) Filed: Oct. 27, 2021

(65) Prior Publication Data
US 2022/0047270 A1 Feb. 17, 2022

Related U.S. Application Data

(63) Continuation of application No. PCT/KR2020/008834, filed on Jul. 7, 2020.

(30) Foreign Application Priority Data

Sep. 2, 2019 (KR) .......................... 10-2019-0108128

(51) Int. Cl.
*A61B 17/12* (2006.01)

(52) U.S. Cl.
CPC .................... *A61B 17/12013* (2013.01); *A61B 2017/12004* (2013.01); *A61B 2017/12018* (2013.01)

(58) Field of Classification Search
CPC .......... A61B 17/12022; A61B 17/0057; A61B 2017/00632; A61B 2017/00637; A61B 2017/00641; A61B 2017/00646; A61B 2017/12159; A61F 13/2054; A61F 13/206; A61F 13/2062; A61F 13/2085;
(Continued)

(56) References Cited

U.S. PATENT DOCUMENTS 3,469,286 A * 9/1969 Crockford ........... A61F 13/2065
28/120
5,807,372 A * 9/1998 Balzar ..................... A61F 13/34
604/385.18
(Continued)

FOREIGN PATENT DOCUMENTS

CN 101801277 A 8/2010
CN 107454851 A 12/2017
(Continued)

*Primary Examiner* — Diane D Yabut
(74) *Attorney, Agent, or Firm* — United One Law Group LLC; Kongsik Kim; Jhongwoo Peck

(57) ABSTRACT

An arthroscopic bleeding control device shows a static absorptive and hemostatic effect against hemorrhage in an articular cavity that can be exposed by an arthroscopy part, and includes a hemostatic block configured to be inserted in the articular cavity through the arthroscopy part, and a hemostatic unit including a lead line extending from the hemostatic block to protrude outside through the arthroscopy part, in which the hemostatic block is formed by winding or folding a hemostatic band elongated in a longitudinal direction and then compressed in a thickness direction at least into a reference thickness for insertion into the articular cavity, so the hemostatic block can be expanded at least in the thickness direction by hemorrhage in the articular cavity, and when the lead line is pulled, the hemostatic band is unwound or unfolded from the expanding hemostatic block, so the hemostatic block is taken out of the articular cavity.

6 Claims, 14 Drawing Sheets

(58) Field of Classification Search
CPC .............. A61F 13/2088; A61F 13/2094; A61F 13/2097; A61F 13/15747; A61F 13/26; A61F 13/263; A61F 13/266; A61F 13/34; A61F 13/36; A61F 2013/4512; A61F 2013/2014

See application file for complete search history.

(56) References Cited

U.S. PATENT DOCUMENTS

| | | |
|---|---|---|
| 6,964,658 B2 | 11/2005 | Ashby et al. |
| 2001/0056254 A1 | 12/2001 | Cragg et al. |

FOREIGN PATENT DOCUMENTS

| | | | |
|---|---|---|---|
| JP | 2012-525930 A | 10/2012 | |
| KR | 10-0947468 B1 | 3/2010 | |
| KR | 10-2019-0009445 A | 1/2019 | |
| KR | 10-2019-0091771 A | 8/2019 | |
| WO | 86/06956 A1 | 12/1986 | |

\* cited by examiner

ARTHROSCOPIC BLEEDING CONTROL DEVICE

CROSS-REFERENCE TO RELATED APPLICATIONS

This application is a Continuation of International Application No. PCT/KR2020/008834 filed on Jul. 7, 2020, which claims priority to Korean Application No. 10-2019-0108128 filed on Sep. 2, 2019. The aforementioned applications are incorporated herein by reference in their entireties.

TECHNICAL FIELD

The present disclosure relates to an arthroscopic bleeding control device and, more particularly, to an arthroscopic bleeding control device that can show a static absorptive and hemostatic effect against hemorrhage in an articular cavity and that can stably take out a hemostatic block expanding by absorbing blood from the articular cavity without a specific tool.

RELATED ART

In general, an arthroscope, which is a kind of endoscope, can directly observe changes in an articular cavity or can take pictures of the changes.

Such an arthroscope makes it possible to make an accurate diagnosis and perform all kinds of surgery related to the inside of joints while directly seeing lesions in the joints through a small-diameter arthroscopy part formed through skin tissues without cutting the joints.

For example, as knee surgery that is possible by an arthroscope, there may be loose body ablation, meniscectomy or meniscal repair, synovectomy, reconstruction of cruciate ligament, etc.

Since an arthroscope does not need to cut a joint, it has many advantages such as less pain after surgery, quick recovery of the ability of a joint, less complication, and reduction of treatment costs, so it can be applied to all joints such as the shoulder, elbow, hand, hip joint, knee, foot, and backbone, and particularly, it is mostly used for the knee joint.

When hemorrhage occurs in an articular cavity during arthroscopy or at the end point in time of arthroscopy, hemostasis is required, but hemostasis is difficult due to a small-diameter arthroscopy part.

As a related art, there is Korean Patent Application Publication No. 10-2019-0091771 (titled, "Hemostatic clip for endoscopy", published on Aug. 7, 2019).

SUMMARY

The present disclosure has been made in an effort to solve the problems in the related art and an objective of the present disclosure is to provide an arthroscopic bleeding control device that can show a static absorptive and hemostatic effect against hemorrhage in an articular cavity and that can stably take out a hemostatic block expanding by absorbing blood from the articular cavity without a specific tool.

In order to achieve the objectives of the present disclosure, according to an exemplary embodiment of the present disclosure, an arthroscopic bleeding control device according to the present disclosure is an arthroscopic bleeding control device that shows a static absorptive and hemostatic effect against hemorrhage in an articular cavity that can be exposed by an arthroscopy part. The arthroscopic bleeding control device includes: a hemostatic block configured to be inserted in the articular cavity through the arthroscopy part; and a hemostatic unit including a lead line extending from the hemostatic block to protrude outside through the arthroscopy part, in which the hemostatic block is formed by winding or folding a hemostatic band elongated in a longitudinal direction and is then compressed in a thickness direction at least into a reference thickness for insertion into the articular cavity, so the hemostatic block can be expanded at least in the thickness direction by hemorrhage in the articular cavity, and when the lead line is pulled, the hemostatic band is unwound or unfolded from the expanding hemostatic block, so the hemostatic block is taken out of the articular cavity.

The lead line is a portion of the hemostatic band extending from the hemostatic block.

The hemostatic block may include: a core forming a spiral center from an end of a hemostatic band; and a spiral wound part formed by spirally winding a hemostatic band extending from the core around the core, the lead line may extend from a free end of a hemostatic band that is finally wound on an outer surface of the spiral wound part, and the core and the spiral wound part may be compressed into the reference thickness in a longitudinal direction of the core.

The core may include: a first core forming a spiral center from an end of a hemostatic band; and a second core coaxially separated from the first core and forming a spiral center from an end of a hemostatic band, the spiral wound part may include: a first wound part formed by spirally winding a hemostatic band extending from the first core around the first core; and a second wound part stacked with the first wound part and formed by spirally winding a hemostatic band extending from the second core around the second core, and the lead line may include: a first lead line extending from a free end of a hemostatic band finally wound on an outer surface of the first wound part; and a second lead line extending from a free end of a hemostatic band finally wound on an outer surface of the second wound part.

The hemostatic block may include: a core forming a spiral center from an end of a hemostatic band; and a spiral wound part formed by spirally winding a hemostatic band extending from the core around the core, the lead line may extend from a free end of the core, and the core and the spiral wound part may be compressed into the reference thickness in a longitudinal direction of the core.

The core may include: a first core forming a spiral center from an end of a hemostatic band; and a second core coaxially separated from the first core and forming a spiral center from an end of a hemostatic band, the spiral wound part may include: a first wound part formed by spirally winding a hemostatic band extending from the first core around the first core; and a second wound part stacked with the first wound part and formed by spirally winding a hemostatic band extending from the second core around the second core, and the lead line may include: a first lead line extending between the first wound part and the second wound part from a free end of the first core; and a second lead line extending between the first wound part and the second wound part from a free end of the second core.

The hemostatic block may include a folding-layered part at which a forward folding portion for folding a hemostatic band toward the lead line in a longitudinal direction of a hemostatic band and a backward folding portion for folding a hemostatic band toward the forward folding portion are alternately disposed and that is layered by folding a hemostatic band in a zigzag pattern; the lead line may extend from the forward folding portion or the backward folding portion formed at any one of both ends of the folding-layered part in a layering direction of a hemostatic band; and the folding-layered part may be compressed into the reference thickness in a layering direction of the hemostatic band.

The lead line may include: a first lead line; and a second lead line disposed to face the first lead line, and the folding-layered part may include: a first layer folded and layered in a zigzag pattern by a forward folding portion and a second folding portion formed at a hemostatic band extending from the first lead line; and a second layer folded and layered in a zigzag pattern by a forward folding portion and a second folding portion formed at a hemostatic band extending from the second lead line.

Lengths of unit layers formed by folding the hemostatic band in a zigzag pattern at the folding-layered part may be all same, or may be sequentially decreased in a layering direction, or may be sequentially decreased in a layering direction.

Assuming that a width of the lead line is W0 and a width of the folding-layered part is W, W/2<=W0<=W may be satisfied.

The hemostatic band may include a spiral folded part formed by sequentially layering a first extension forming a portion of the hemostatic band, a second extension layered on the end of the first extension to cross the first extension, a third extension layered on the end of the second extension to cross the second extension and to be parallel with the first extension, a fourth extension layered on the end of the third extension to cross the third extension and the first extension and to be parallel with the second extension, and a fifth extension crossing the fourth extension and layered on the first extension; the lead line may extend from the first extension; and the spiral folded part may be compressed into the reference thickness in a layering direction of a hemostatic band.

The lead line may include: a first lead line; and a second lead line disposed to face the first lead line, and the spiral folded part may include: a first spiral part at which a first extension extending from the first lead line, a second extension, and a third extension are sequentially layered; and a second spiral part at which a first extension extending from the second lead line, a second extension, and a third extension are sequentially layered.

Assuming that a width of the lead line is W0 and a width of the folding-layered part is W, W=W0/2 may be satisfied.

The arthroscopic bleeding control device may further include a block insertion unit configured to insert the hemostatic block into the articular cavity.

The block insertion unit may include: a block guide unit that forms a passage for inserting the hemostatic block into the articular cavity and in which the hemostatic block is inserted; and a block transfer unit fitted in a first side of the block guide unit and configured to take out the hemostatic block through a second side of the block guide unit using external force.

The block guide unit may include: a hollow sheath tube in which the hemostatic block is inserted and in which the block transfer unit is slidably fitted at a first side; and a guide blade that has elasticity and closes a second side of the sheath tube, and the guide blade may open the second side of the sheath tube by elastically deforming when the hemostatic block is slid.

According to the arthroscopic bleeding control device of the present disclosure, there is a static absorptive and hemostatic effect against hemorrhage in the articular cavity and it is possible to stably take out the hemostatic block expanding by absorbing blood from the articular cavity without a specific tool.

Further, since the hemostatic unit is composed of one hemostatic band, the hemostatic unit can be implemented as a single part and the hemostatic block can be simply fabricated.

Further, according to the detailed configuration of the hemostatic unit, the hemostatic block can be formed in a cylindrical shape or an elliptical cylindrical unit and the thickness of the hemostatic block can be simply adjusted.

Further, according to the detailed configuration of the hemostatic unit, it is possible to minimize rubbing due to the hemostatic band in the articular cavity or the arthroscopy part when unwinding the hemostatic block.

Further, according to the detailed configuration of the hemostatic unit, the hemostatic block can be formed in a rectangular prism shape, the length of the hemostatic block is easily adjusted, and the hemostatic band is taken out in a flat state from the articular cavity or the arthroscopy part and rubbing by the hemostatic band can be minimized when the hemostatic block is unfolded.

Further, according to the detailed configuration of the hemostatic unit, the hemostatic block can be formed in a hexagonal prism or rhombus prism shape, the length of the hemostatic block is easily adjusted, and the hemostatic band is taken out in a rolled state and rubbing by the hemostatic band in the articular cavity or the arthroscopy part can be minimized when the hemostatic block is unfolded.

Further, the hemostatic block of the hemostatic unit is divided into two parts and the hemostatic band is taken out from between the divided hemostatic block, so rubbing by the hemostatic band in the articular cavity or the arthroscopy part can be minimized.

Further, it is possible to adjust the size of the hemostatic block in the articular cavity using the relationship between the width of the lead line and the folding-layered part.

Further, it is possible to stably insert the hemostatic block into the articular cavity through the block insertion unit.

Further, according to the detailed configuration of the block insertion unit, it is possible to stably guide the hemostatic block inserted in the block guide unit 61 in position in the articular cavity.

Further, according to the detailed configuration of the block guide unit, when the block guide unit is inserted into the arthroscopy part, rubbing by the block guide unit in the arthroscopy part is prevented and the hemostatic block is stably taken out through the second side of the block guide unit. Further, when the block guide unit is taken out, it is possible to prevent the guide blade from rubbing the arthroscopy part.

DETAILED DESCRIPTION

Figure 1:
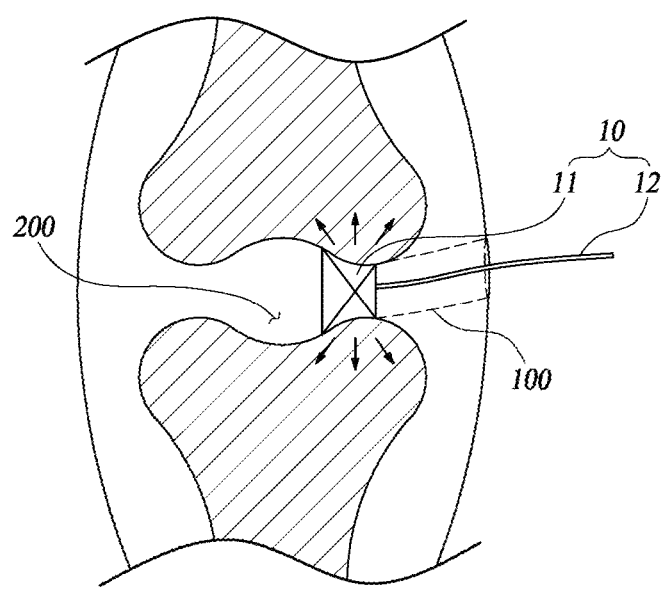
FIG. 1 is a view showing the state in which a hemostatic block of an arthroscopic bleeding control device according to an embodiment of the present disclosure has been inserted in an articular cavity through an arthroscopy part.

An embodiment of an arthroscopic bleeding control device according to an embodiment of the present disclosure is described hereafter with reference to the accompanying drawings. However, the present disclosure is not restricted or limited by the embodiment of the present disclosure. In the following description of the present disclosure, well-known functions or configurations may not be described in detail to make the subject of the present disclosure clear.

Referring to FIGS. 1 to 14, an arthroscopic bleeding control device according to an embodiment of the present disclosure, which is a device showing a static absorptive and hemostatic effect against hemorrhage in an articular cavity that is exposed by an arthroscopy part 100, includes a hemostatic unit 10 and may further include a block insertion unit 60.

The hemostatic unit 10 includes a hemostatic block 11 that is inserted into an articular cavity 200 through the arthroscopy part 100, and a lead line 12 extending from the hemostatic block 11 to protrude outside through the arthroscopy part 100.

The hemostatic block 11 is formed by winding or folding a hemostatic band 101 elongated in the longitudinal direction and then compressed in the thickness direction at least into a reference thickness T for insertion into the articular cavity 200. The compressed hemostatic block 11 absorbs blood coming out in the articular cavity 200, so it can expand at least in the thickness direction due to hemorrhage. Body fluid produced in the articular cavity 200 may be contained in the blood coming out in the articular cavity 200.

The lead line 12 is a part of the hemostatic band 101 extending from the hemostatic block 11 and also can absorb blood. Lubrication is generated between the arthroscopy part 100 and the hemostatic band 101 by the blood absorbed in the hemostatic band 101, whereby the hemostatic band 101 can be smoothly taken out.

When the hemostatic block 11 absorbs blood in the articular cavity 200 and the lead line 12 is pulled, the hemostatic band 101 is unwound or unfolded from the expanding hemostatic block 11, so the hemostatic block 11 can be taken out of the articular cavity 200.

Figure 2:
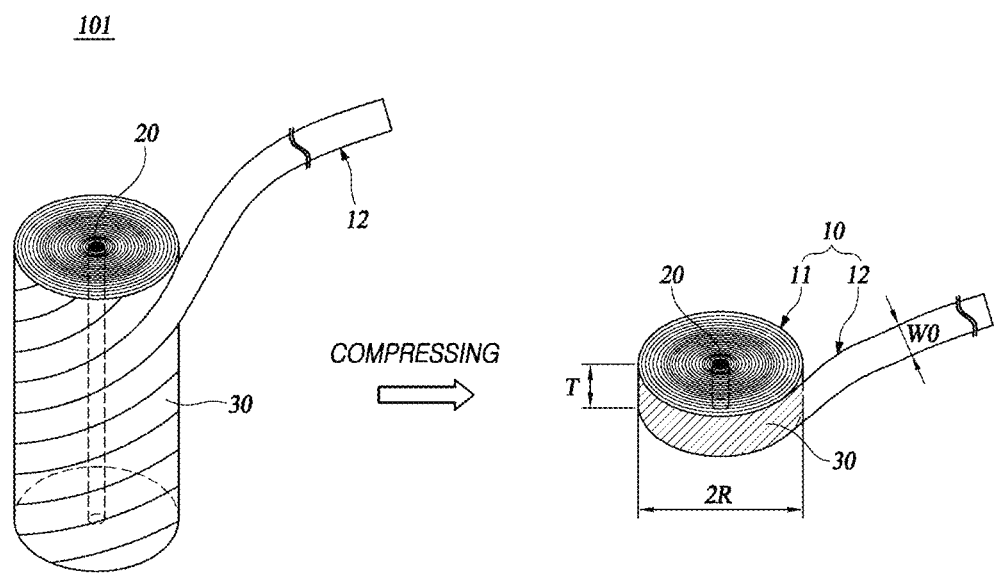
FIG. 2 is a view showing a first embodiment of a hemostatic unit of the arthroscopic bleeding control device according to an embodiment of the present disclosure, in which a hemostatic block has been wound and the hemostatic unit has been completed.

The hemostatic unit 10 according to a first embodiment, as shown in FIG. 2, may include the hemostatic block 11 and the lead line 12.

In the first embodiment, the hemostatic block 11 may include a core 20 forming a spiral center from an end of the hemostatic band 101, and a spiral wound part 30 formed by spirally winding the hemostatic band 101 extending from the core 20 around the core 20.

The core 20 may be formed by making a portion of the hemostatic band 101 straight, or winding or rolling a portion of the hemostatic band 101.

The core 20 and the spiral wound part 30 are compressed into the reference thickness T in the longitudinal direction of the winding shaft 20, whereby the hemostatic block 11 can be completed.

In the first embodiment, the lead line 12 may extend from the free end of the hemostatic band 101 that is finally wound on the outer surface of the spiral wound part 30.

According to the first embodiment, when the lead line 12 is pulled, the hemostatic block 11 is rotated and the hemostatic band 101 is taken out, whereby foreign substances can be swept out of the articular cavity 200.

Although the hemostatic block 11 is formed in a cylindrical shape in the first embodiment, it is not limited thereto and may be formed in an elliptical cylindrical shape.

Assuming that the width of the lead line 12 is W0 and the reference thickness is T for the hemostatic block 11 having a cylindrical shape, T=W0 can be satisfied. In other words, it can be satisfied that T and W0 are substantially the same. The diameter of the hemostatic block 11 can satisfy 2R with respect to the width of the articular cavity 200. R is the radius of the spiral wound part 30 from the core 20.

Figure 3:
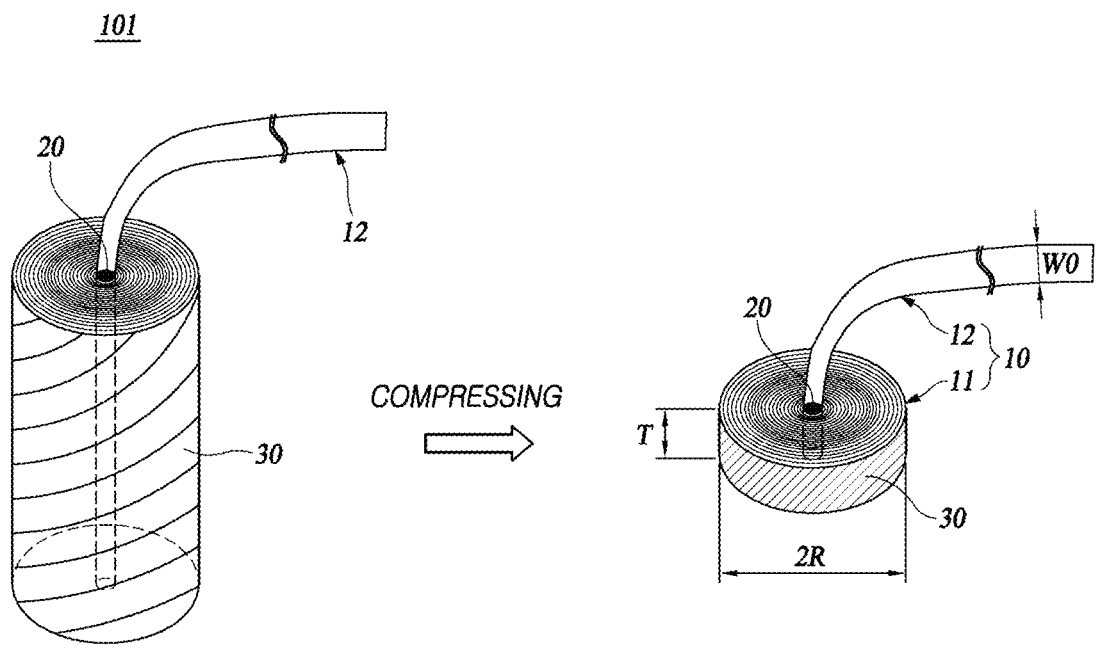
FIG. 3 is a view showing a second embodiment of a hemostatic unit of the arthroscopic bleeding control device according to an embodiment of the present disclosure, in which a hemostatic block has been wound and the hemostatic unit has been completed.
Figure 4:
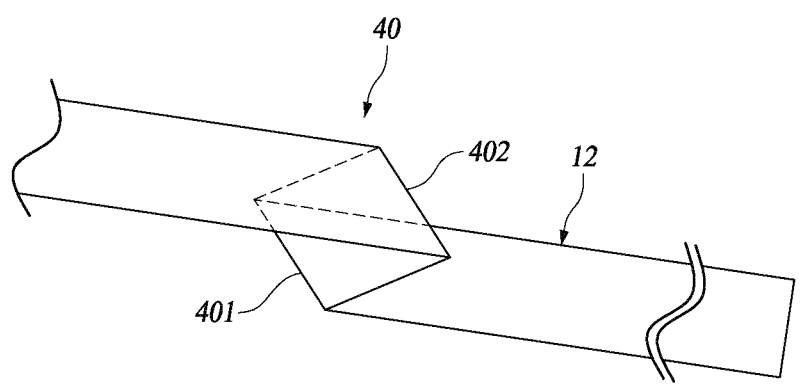
FIG. 4 is a view showing a third embodiment of a hemostatic unit of the arthroscopic bleeding control device according to an embodiment of the present disclosure, in which a method of folding the hemostatic block is shown.

A hemostatic unit 10 according to a second embodiment, as shown in FIG. 3, may include a hemostatic block 11 and a lead line 12.

In the second embodiment, the hemostatic block 11 may include a core 20 forming a spiral center from an end of the hemostatic band 101, and a spiral wound part 30 formed by spirally winding the hemostatic band 101 extending from the core 20 around the core 20.

The core 20 may be formed by making a portion of the hemostatic band 101 straight, or winding or rolling a portion of the hemostatic band 101.

The core 20 and the spiral wound part 30 are compressed into the reference thickness T in the longitudinal direction of the winding shaft 20, whereby the hemostatic block 11 can be completed.

In the second embodiment, the lead line 12 may extend from the free end of the core 20.

According to the second embodiment, when the lead line 12 is pulled, the hemostatic band 101 is taken out from the center of the hemostatic block 11, so it is possible to prevent friction with the hemostatic band 101 in the articular cavity 200 and it is also possible to minimize rubbing due to rolling of the hemostatic band 101, which is taken out from the hemostatic block 11, by minimizing friction with the hemostatic band 101 at the arthroscopy part 100.

Although the hemostatic block 11 is formed in a cylindrical shape in the second embodiment, it is not limited thereto and may be formed in an elliptical cylindrical shape.

Assuming that the width of the lead line 12 is W0 and the reference thickness is T for the hemostatic block 11 having a cylindrical shape, T=W0 can be satisfied. In other words, it can be satisfied that T and W0 are actually the same. The diameter of the hemostatic block 11 can satisfy 2R with respect to the width of the articular cavity 200. R is the radius of the spiral wound part 30 from the core 20.

A hemostatic unit 10 according to a third embodiment, as shown in FIGS. 4 to 7, may include a hemostatic block 11 and a lead line 12.

In the third embodiment, the hemostatic block 11 may have a folding-layered part 40 at which a forward folding portion 401 and a backward folding portion 402 are alternately disposed in the longitudinal direction of the hemostatic band 101 and that is formed by folding the hemostatic band 101 in a zigzag pattern in correspondence to the forward folding portion 401 and the backward folding portion 402. The forward folding portion 401 may be a crease for folding the hemostatic band 101 toward the lead line 12 and the backward folding portion 402 may be a crease spaced apart from the forward folding portion 401 and provided to fold the hemostatic band 101 toward the forward folding portion 401.

When the hemostatic band 101 is folded in a zigzag pattern at the folding-layered part 40, a unit layer is formed by the forward folding portion 401 and the backward folding portion 402 that are adjacent to each other, so it can be seen that the unit layers are sequentially formed from the lead line 12. The lengths of the unit layer formed by folding the hemostatic band 101 in a zigzag pattern at the folding-layered part 40 may be all the same, may be sequentially decreased in the layering direction, or may be sequentially increased in the layering direction.

Figure 5:
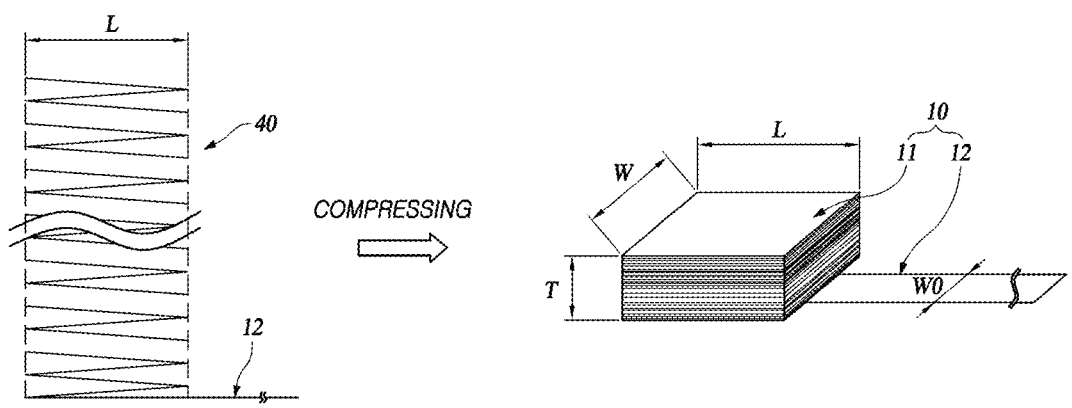
FIG. 5 is a view showing the third embodiment of a hemostatic unit of the arthroscopic bleeding control device according to an embodiment of the present disclosure, in which the hemostatic block according to a first modified example has been folded and a hemostatic unit has been completed in accordance with the first modified example.

In a first modified example, the lengths of the unit layers, as shown in FIG. 5, may be substantially the same in the layering direction from the lead line 12.

Figure 6:
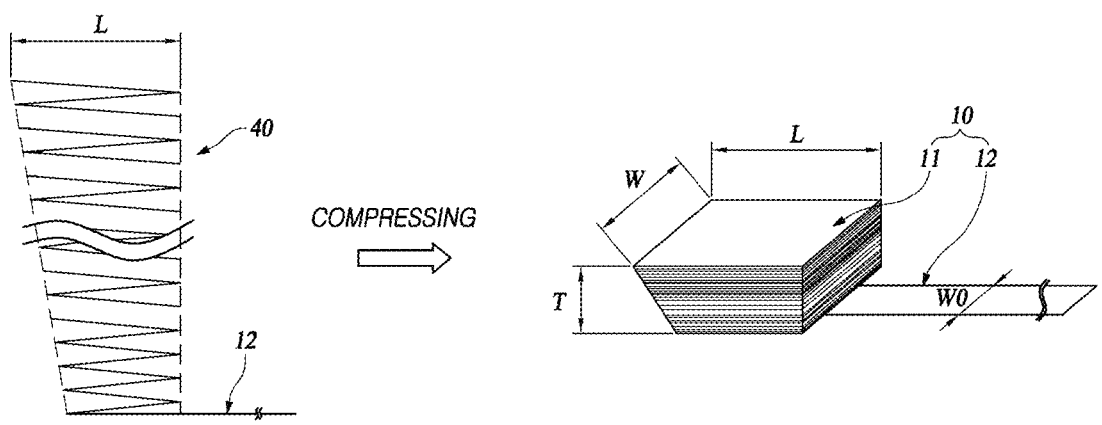
FIG. 6 is a view showing the third embodiment of a hemostatic unit of the arthroscopic bleeding control device according to an embodiment of the present disclosure, in which the hemostatic block according to a second modified example has been folded and a hemostatic unit has been completed in accordance with the second modified example.

In a second modified example, the lengths of the unit layers, as shown in FIG. 6, may be gradually increased in the layering direction from the lead line 12.

Figure 7:
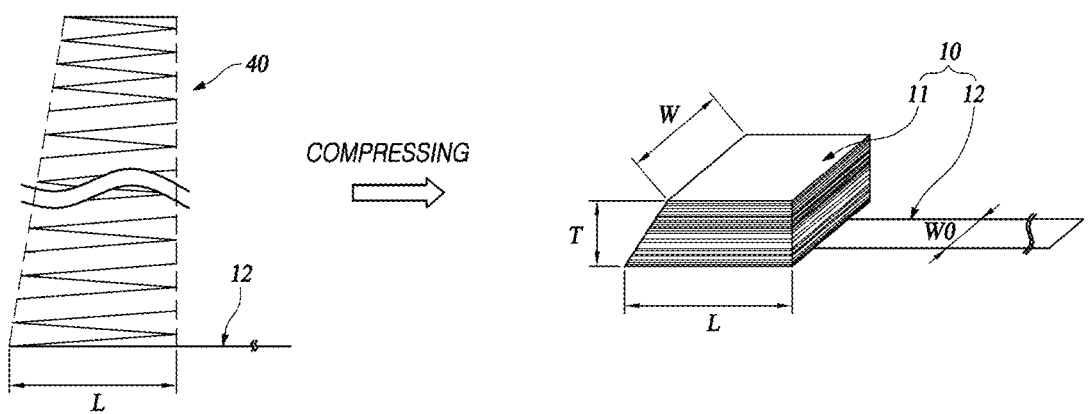
FIG. 7 is a view showing the third embodiment of a hemostatic unit of the arthroscopic bleeding control device according to an embodiment of the present disclosure, in which the hemostatic block according to a third modified example has been folded and a hemostatic unit has been completed in accordance with the third modified example.

In a third modified example, the lengths of the unit layers, as shown in FIG. 7, may be gradually decreased in the layering direction from the lead line 12.

The folding-layered part 40 may be compressed into a reference thickness T in the layering direction of the hemostatic band 101, whereby the hemostatic block 11 can be completed.

In the third embodiment, the lead line 12 may extend from the forward folded portion 401 or the backward folded portion 402 that is formed at any one of both ends of the folding-layered part 40 in the layering direction of the hemostatic band 101. Accordingly, the lead line 12 may extend from the lower end or the upper end of the hemostatic block 11.

According to the third embodiment, when the lead line 12 is pulled, the hemostatic band 101 is sequentially taken out from the lower end or the upper end of the hemostatic block 11 inserted in the articular cavity 200 in accordance with the stack of the hemostatic band 101. Accordingly, it is possible to reduce friction between the hemostatic band 101 and the articular cavity 200 and friction between the hemostatic band 101 and the arthroscopy part 100.

In the third embodiment, the hemostatic block 11 may be formed in a rectangular prism shape.

Assuming that the width of the lead line 12 is W0 and the width of the folding-layered part 40 is W for the hemostatic block 11 having a rectangular prism shape, W/2<=W0<=W can be satisfied. In other words, it can be satisfied that W0 is a half or more of W and is equal to or less than W. In this case, the reference thickness T is constant and the length of the hemostatic block 11 can be adjusted in accordance with the distance between the forward folded portion 401 and the backward folded portion 402.

Figure 8:
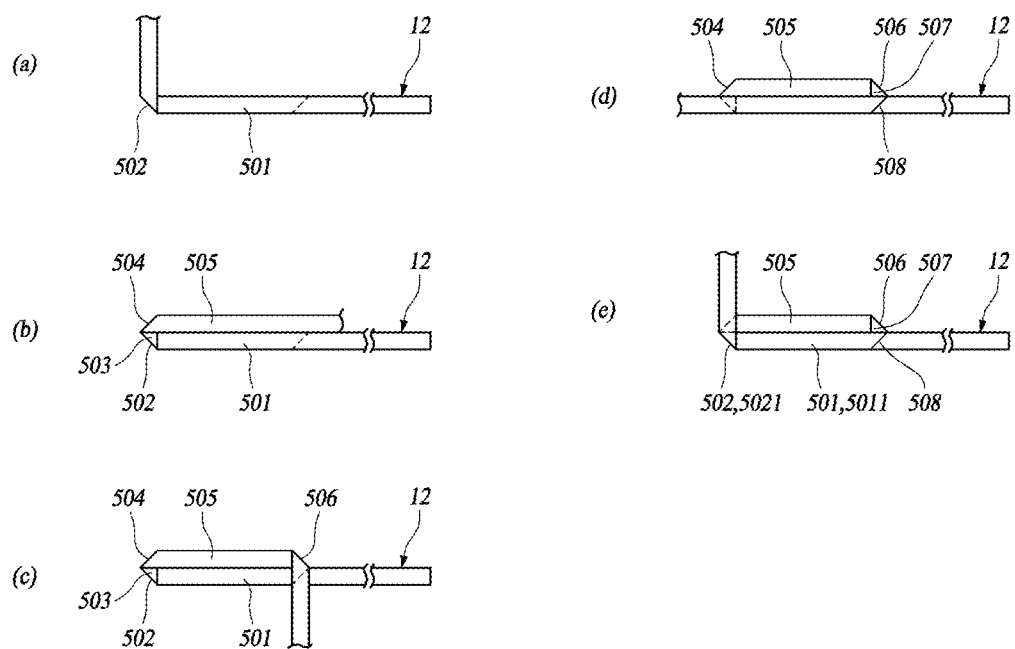
FIG. 8 is a view showing a fourth embodiment of a hemostatic unit of the arthroscopic bleeding control device according to an embodiment of the present disclosure, in which a method of folding the hemostatic block is shown.
Figure 9:
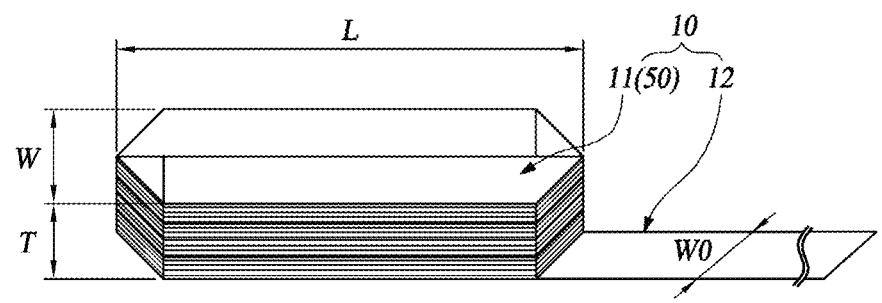
FIG. 9 is a view showing the fourth embodiment of a hemostatic unit of the arthroscopic bleeding control device according to an embodiment of the present disclosure, in which a completed hemostatic unit is shown.

A hemostatic unit 10 according to a fourth embodiment, as shown in FIGS. 8 and 9, may include a hemostatic block 11 and a lead line 12.

In the fourth embodiment, the hemostatic block 11 may have a spiral folded part 50 formed by sequentially layering a first extension 501 forming a portion of the hemostatic band 101, a second extension 503 layered on the end of the first extension 501 to cross the first extension 501, a third extension 505 layered on the end of the second extension 503 to cross the second extension 503 and to be parallel with the first extension 501, a fourth extension 507 layered on the end of the third extension 505 to cross the third extension 505 and the first extension 501 and to be parallel with the second extension 503, and a fifth extension 5011 crossing the fourth extension 507 and layered on the first extension 501.

The crease connecting the first extension 501 and the second extension 503 is referred to as a first forward inclined portion 502, the crease connecting the second extension 503 and the third extension 505 is referred to as a first backward inclined portion 504, the crease connecting the third extension 505 and the fourth extension 507 is referred to as a first forward inclined portion 502, the crease connecting the fourth extension 507 and the fifth extension 5011 is referred to as a second backward inclined portion 508, and the crease for folding from the fifth extension 5011 when the hemostatic band 101 is additionally layered on the second extension 503 is referred to as a third forward inclined portion 5021.

The spiral folded part 50 is compressed into a reference thickness T in the layering direction of the hemostatic band 101, whereby the hemostatic block 11 can be completed.

In the fourth embodiment, the lead line 12 may extend from the first extension 501. Accordingly, the lead line 12 may extend from the lower end or the upper end of the hemostatic block 11.

According to the fourth embodiment, when the lead line 12 is pulled, the hemostatic band 101 is sequentially rolled and taken out from the lower end or the upper end of the hemostatic block 11 inserted in the articular cavity 200 in accordance with the stack of the hemostatic band 101. Accordingly, it is possible to reduce friction between the hemostatic band 101 and the articular cavity 200 and friction between the hemostatic band 101 and the arthroscopy part 100.

In the fourth embodiment, the hemostatic block 11 may be formed in a hexagonal prism or rhombic prism shape.

Assuming that the width of the lead line 12 is W0 and the width of the folding-layered part 40 (the sum of the width of the first extension 501 and the width of the third extension 505) is W for the hemostatic block 11 having a hexagonal prism shape, W=W0/2 can be satisfied. In other words, it can be satisfied that W is substantially the same as a half of W0. In this case, the reference thickness T is constant and the length of the hemostatic block 11 can be adjusted in accordance with the lengths of the first extension 501 and the third extension 505.

Figure 10:
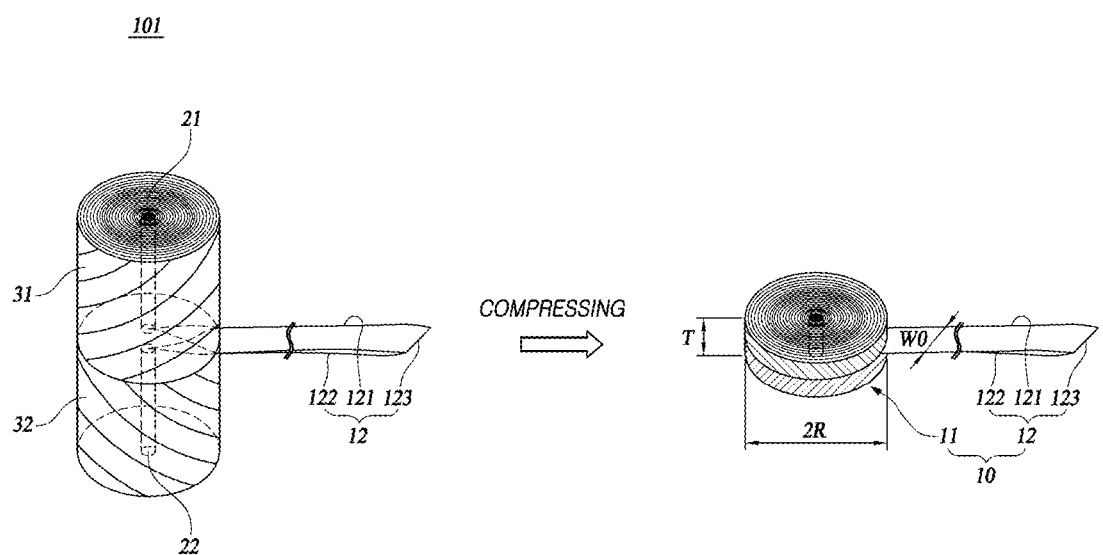
FIG. 10 is a view showing a fifth embodiment of a hemostatic unit of the arthroscopic bleeding control device according to an embodiment of the present disclosure, in which a hemostatic block has been wound and the hemostatic unit has been completed.

A hemostatic unit 10 according to a fifth embodiment, as shown in FIG. 10, may include a hemostatic block 11 and a lead line 12.

The hemostatic block 11, as in the second embodiment, may include a core 20 forming a spiral center from an end of the hemostatic band 101, and a spiral wound part 30 formed by spirally winding the hemostatic band 101 extending from the core 20 around the core 20.

In the fifth embodiment, the core 20 may include a first core 21 forming a spiral center from an end of the hemostatic band 101 and a second core 22 coaxially separated from the first core 21 and forming a spiral center from the end of the hemostatic band 101.

The first core 21 and the second core 22 each may be formed by making a portion of the hemostatic band 101 straight, or winding or rolling a portion of the hemostatic band 101.

In the fifth embodiment, the spiral wound part 30 may include a first wound part 31 formed by spirally winding the hemostatic band 101 extending from the first core 21 around the first core 21, and a second wound part 32 stacked with the first wound part 31 and formed by spirally winding the hemostatic band 101 extending from the second core 22 around the second core 22. Although the first wound part 31 and the second wound part 32 are spirally formed in opposite directions, they may be spirally wound in the same direction.

The first core 21, the first wound part 31, the second core 22, and the second wound part 32 are compressed into a reference thickness T in the longitudinal direction of the first core 21 or the longitudinal direction of the second core 22, whereby the hemostatic block 11 can be completed.

In the fifth embodiment, the lead line 12 may include a first lead line 121 extending between the first wound part 31 and the second wound part 32 from a free end of the first core 21, and a second lead line 122 extending between the first wound part 31 and the second wound part 32 from a free end of the second core 22. The lead line 12 may further include a connecting portion 123 integrally connecting a free end of the first lead line 121 and a free end of the second lead line 122, whereby the lead line 12 can have a ring shape and a user can conveniently hold the lead line 12.

According to the fifth embodiment, when the first lead line 121 and the second lead line 122 are pulled, the hemostatic band 101 is taken out from the center of the hemostatic block 11 between the first wound part 31 and the second wound part 32, so it is possible to prevent friction with the hemostatic band 101 in the articular cavity 200 and it is also possible to minimize rubbing due to rolling of the hemostatic band 101, which is unwound from the hemostatic block 11, by minimizing friction with the hemostatic band 101 at the arthroscopy part 100.

Although the hemostatic block 11 is formed in a cylindrical shape in the fifth embodiment, it is not limited thereto and may be formed in an elliptical cylindrical shape.

Assuming that the width of the lead line 12 is W0 and the reference thickness is T for the hemostatic block 11 having a cylindrical shape, T=W0 can be satisfied. In other words, it can be satisfied that T and W0 are substantially the same. The diameter of the hemostatic block 11 can satisfy 2R with respect to the width of the articular cavity 200. R is the radius of the spiral wound part 30 from the core 20.

Though not shown, a hemostatic unit 10, as in the first embodiment, may include a core 20 forming a spiral center from an end of the hemostatic band 101, and a spiral wound part 30 formed by spirally winding the hemostatic band 101 extending from the core 20 around the core 20.

The core 20 may include a first core 21 forming a spiral center from an end of the hemostatic band 101 and a second core 22 coaxially separated from the first core 21 and forming a spiral center from the end of the hemostatic band 101.

The first core 21 and the second core 22 each may be formed by making a portion of the hemostatic band 101 straight, or winding or rolling a portion of the hemostatic band 101.

The spiral wound part 30 may include a first wound part 31 formed by spirally winding the hemostatic band 101 extending from the first core 21 around the first core 21, and a second wound part 32 stacked with the first wound part 31 and formed by spirally winding the hemostatic band 101 extending from the second core 22 around the second core 22.

The first core 21, the first wound part 31, the second core 22, and the second wound part 32 are compressed into a reference thickness T in the longitudinal direction of the first core 21 or the longitudinal direction of the second core 22, whereby the hemostatic block 11 can be completed.

The lead line 12 may include a first lead line 121 extending from a free end of the hemostatic band 101 finally wound on the outer surface of the first wound part 31, and a second lead line 122 extending from a free end of the hemostatic band 101 finally wound on the outer surface of the second wound part 32. The lead line 12 may further include a connecting portion 123 integrally connecting a free end of the first lead line 121 and a free end of the second lead line 122, whereby the lead line 12 can have a ring shape and a user can conveniently hold the lead line 12.

When the lead line 12 is pulled from a hemostatic unit 10 not shown, the hemostatic block 11 can be taken out while rotating. Since the first wound part 31 and the second wound part 32 are spirally wound in opposite directions, the first wound part 31 and the second wound part 32 can be positioned adjacent to each other and the hemostatic block 11 can be smoothly rotated.

Accordingly, the hemostatic block 11 may be a cylindrical shape or an elliptical cylindrical shape.

Figure 11:
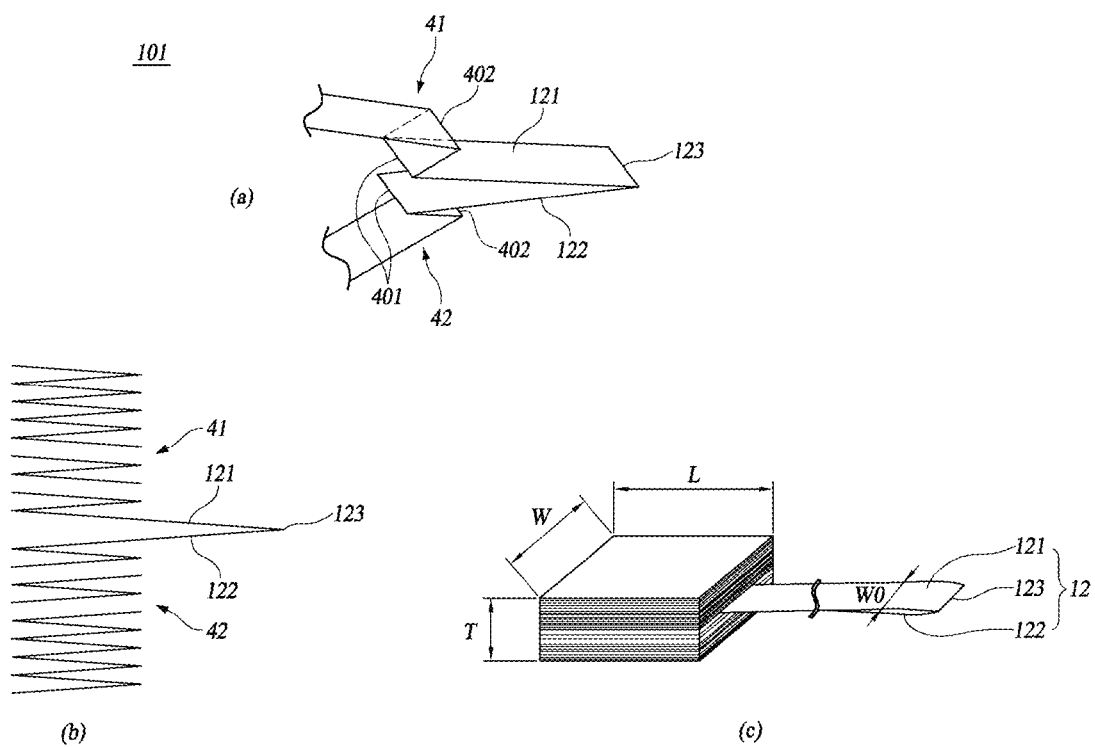
FIG. 11 is a view showing a sixth embodiment of a hemostatic unit of the arthroscopic bleeding control device according to an embodiment of the present disclosure, in which (a) shows a method of folding a hemostatic block, (b) shows the folded state of the hemostatic block, and (c) shows a completed hemostatic unit.

A hemostatic unit 10 according to a sixth embodiment, as shown in FIG. 11, may include a hemostatic block 11 and a lead line 12.

The hemostatic block 11, as in the third embodiment, may have a folding-layered part 40 at which a forward folding portion 401 and a backward folding portion 402 are alternately disposed in the longitudinal direction of the hemostatic band 101 and that is formed by folding the hemostatic band 101 in a zigzag pattern in correspondence to the forward folding portion 401 and the backward folding portion 402. The forward folding portion 401 may be a crease for folding the hemostatic band 101 toward the lead line 12 and the backward folding portion 402 may be a crease spaced apart from the forward folding portion 401 and provided to fold the hemostatic band 101 toward the forward folding portion 401.

When the hemostatic band 101 is folded in a zigzag pattern at the folding-layered part 40, a unit layer is formed by the forward folding portion 401 and the backward folding portion 402 that are adjacent to each other, so it can be seen that the unit layers are sequentially formed from the lead line 12. The lengths of the unit layers formed by folding the hemostatic band 101 in a zigzag pattern at the folding-layered part 40 may be all the same, may be sequentially decreased in the layering direction, or may be sequentially increased in the layering direction.

The lead line 12, as in the third embodiment, may extend from the forward folded portion 401 or the backward folded portion 402 that is formed at any one of both ends of the folding-layered part 40 in the layering direction of the hemostatic band 101.

In the sixth embodiment, the lead line 12 may include a first lead line 121 and a second lead line 122 disposed to face the first lead line 121. The lead line 12 may further include a connecting portion 123 integrally connecting a free end of the first lead line 121 and a free end of the second lead line 122, whereby the lead line 12 can have a ring shape and a user can conveniently hold the lead line 12.

In the sixth embodiment, the folding-layered part 40 may include a first layer 41 folded and layered in a zigzag pattern by a forward folding portion 401 and a second folding portion 402 formed at the hemostatic band 101 extending from the first lead line 121, and a second layer 42 folded and layered in a zigzag pattern by a forward folding portion 401 and a second folding portion 402 formed at the hemostatic band 101 extending from the second lead line 121.

The first layer 41 and the second layer 42 are compressed into a reference thickness T in the layering direction of the hemostatic band 101, whereby the hemostatic block 11 can be completed.

According to the sixth embodiment, when the first lead line 121 and the second lead line 122 are pulled, the hemostatic band 101 is sequentially taken out from the middle portion of the hemostatic block 11 between the first layer 41 and the second layer 42, so it is possible to prevent friction with the hemostatic band 101 in the articular cavity 200 and it is also possible to reduce friction between the hemostatic band 101 and the arthroscopy part 100.

In the sixth embodiment, the hemostatic block 11 may be formed in a rectangular prism shape.

Assuming that the width of the lead line 12 is W0 and the width of the folding-layered part 40 is W for the hemostatic block 11 having a rectangular prism shape, W/2<=W0<=W can be satisfied. In other words, it can be satisfied that W0 is a half or more of W and is equal to or less than W. In this case, the reference thickness T is constant and the length of the hemostatic block 11 can be adjusted in accordance with the distance between the forward folded portion 401 and the backward folded portion 402.

Figure 12:
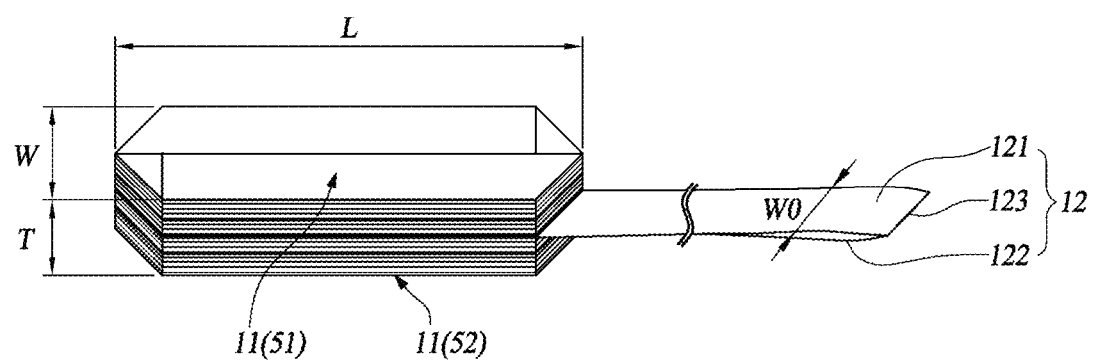
FIG. 12 is a view showing a seventh embodiment of a hemostatic unit of the arthroscopic bleeding control device according to an embodiment of the present disclosure, in which a completed hemostatic unit is shown.

A hemostatic unit 10 according to a seventh embodiment, as shown in FIG. 12, may include a hemostatic block 11 and a lead line 12.

The hemostatic block 11, as in the fourth embodiment, may have a spiral folded part 50 formed by sequentially layering a first extension 501 forming a portion of the hemostatic band 101, a second extension 503 layered on the end of the first extension 501 to cross the first extension 501, a third extension 505 layered on the end of the second extension 503 to cross the second extension 503 and to be parallel with the first extension 501, a fourth extension 507 layered on the end of the third extension 505 to cross the third extension 505 and the first extension 501 and to be parallel with the second extension 503, and a fifth extension 5011 crossing the fourth extension 507 and layered on the first extension 501.

The lead line 12, in the fourth embodiment, may extend from the first extension 501.

In the seventh embodiment, the lead line 12 may include a first lead line 121 and a second lead line 122 disposed to face the first lead line 121. The lead line 12 may further include a connecting portion 123 integrally connecting a free end of the first lead line 121 and a free end of the second lead line 122, whereby the lead line 12 can have a ring shape and a user can conveniently hold the lead line 12.

In the seventh embodiment, the spiral folded part 50 may include: a first spiral part 51 at which the first extension 501 extending from the first lead line 121, the second extension 503, the third extension 505, the fourth extension 507, and the fifth extension 5011 are sequentially layered; and a second spiral part 52 at which the first extension 501 extending from the second lead line 122, the second extension 503, the third extension 505, the fourth extension 507, and the fifth extension 5011 are sequentially layered.

The first spiral part 51 and the second spiral part 52 are compressed into a reference thickness T in the layering direction of the hemostatic band 101, whereby the hemostatic block 11 can be completed.

According to the seventh embodiment, when the first lead line 121 and the second lead line 122 are pulled, the hemostatic band 101 is sequentially taken out while being rolled from the middle portion of the hemostatic block 11 between the first spiral part 51 and the second spiral part 52, so it is possible to prevent friction between the hemostatic band 101 and the articular cavity 200 and it is also possible to reduce friction between the hemostatic band 101 and the arthroscopy part 100.

In the seventh embodiment, the hemostatic band 11 may be formed in a hexagonal prism or rhombic prism shape.

Assuming that the width of the lead line 12 is W0 and the width of the folding-layered part 40 (the sum of the width of the first extension 501 and the width of the third extension 505) is W for the hemostatic block 11 having a hexagonal prism shape, W=W0/2 can be satisfied. In other words, it can be satisfied that W is substantially the same as a half of W0. In this case, the reference thickness T is constant and the length of the hemostatic block 11 can be adjusted in accordance with the lengths of the first extension 501 and the third extension 505.

Figure 13:
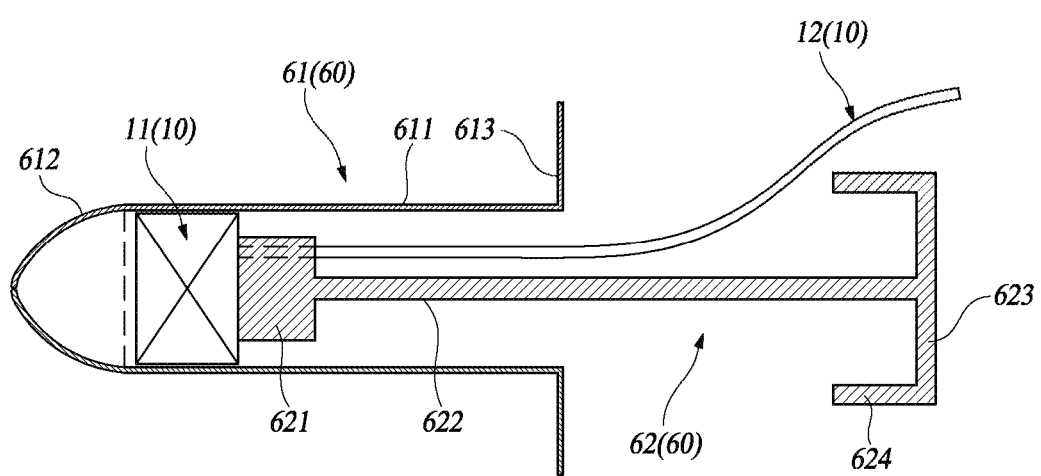
FIG. 13 is a cross-sectional view showing a coupled state of a hemostatic unit and a block insertion unit in the arthroscopic bleeding control device according to an embodiment of the present disclosure.
Figure 14:
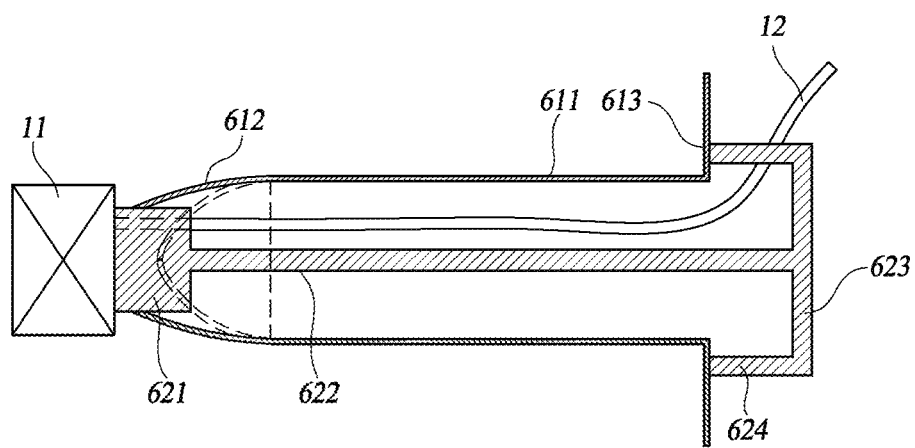
FIG. 14 is a cross-sectional view showing the state in which the hemostatic block has been taken out of the block insertion unit in the arthroscopic bleeding control device according to an embodiment of the present disclosure.

A block insertion unit 60 inserts the hemostatic block 11 into the articular cavity 200. As shown in FIGS. 13 and 14, the block insertion unit 60 may include a block guide unit 61 forming a passage through which the hemostatic block 11 is inserted into the articular cavity 200, and a block transfer unit 62 that takes out the hemostatic block 11 from the block guide unit 61 using external force.

The hemostatic block 11 is inserted in the block guide unit 61 and lead line 12 protrudes through a first side of the block guide unit 61.

The block guide unit 61 may include a hollow sheath tube 611 in which the hemostatic block 11 is inserted, and a guide blade 612 having elasticity and closing a second side of the sheath tube 611. The block transfer unit 62 may be slidably fitted in a first side of the sheath tube 611. When the hemostatic block 11 is slid, the guide blade 612 elastically deforms and opens the second side of the sheath tube 611 so that the hemostatic block 11 can be taken out through the second side of the sheath tube 611.

The block guide unit 61 may further include a grip blade 613 disposed at the first side of the sheath tube 611 to be held by a user.

The block transfer unit 62 is fitted from the first side of the block guide unit 61 without interfering with the lead line 12.

The block transfer unit 62 may include a transfer piston 621 slidably fitted in the sheath tube 611 of the block guide unit 61, a transfer rod 622 extending from the transfer piston 621 to protrude from the first side of the sheath tube 611, and a pusher 623 disposed at a free end of the transfer rod 622 for pressing by a user.

The block transfer unit 62 may further include a stopper 624 that restricts sliding of the transfer piston 621. For example, the stopper 624 protrudes from the pusher 623 to be supported by a first end of the sheath tube 611 or the grip blade 613, and can prevent the transfer piston 621 from coming out of the block guide unit 61 when the transfer piston 621 pushes out the hemostatic block 11 through the second side of the block guide unit 621.

Accordingly, when a user inserts the block guide unit 61 into the arthroscopy part 100 and then presses the pusher 623 while holding the first side of the sheath tube 611 or the grip blade 613, the transfer piston 621 slides the hemostatic block 11 inserted in the sheath tube 611. In this process, since the hemostatic block 11 presses the guide blade 612 at the second side of the sheath tube 611, the hemostatic block 11 opens the second side of the sheath tube 611 by elastically opening the guide blade 612 and keeps moving to come out through the second side of the sheath tube 611, whereby the hemostatic block 11 is inserted into the articular cavity 200.

In this process, the stopper 624 is supported by the first end of the sheath tube 611 or the grip blade 613, so the transfer piston 621 is supported by the guide blade 612 without coming out through the second side of the sheath tube 611.

When blood is absorbed in the hemostatic block 11, it is possible to take out the hemostatic block 11 from the articular cavity 200 by pulling lead line 12, depending on whether the block guide unit 61 is inside the arthroscopy part 100 or the block guide unit 61 is outside the arthroscopy part 100.

For example, when the block guide unit 61 is inside the arthroscopy part 100, the transfer piston 621 supports the guide blade 612 and the lead line 12 passes through between the transfer piston 621 and the guide blade 612, so interference with the hemostatic band 101 by the block guide unit 61 can be prevented.

According to the arthroscopic bleeding control device described above, there is a static absorptive and hemostatic effect against hemorrhage in the articular cavity 200 and it is possible to stably take out the hemostatic block 11 expanding by absorbing blood from the articular cavity 200 without a specific tool.

Further, since the hemostatic unit 10 is composed of one hemostatic band 101, the hemostatic unit 10 can be implemented as a single part and the hemostatic block 11 can be simply fabricated.

Further, according to the detailed configuration of the hemostatic unit 10, the hemostatic block 11 can be formed in a cylindrical shape or an elliptical cylindrical unit and the thickness of the hemostatic block 11 can be simply adjusted.

Further, according to the detailed configuration of the hemostatic unit 10, it is possible to minimize rubbing due to the hemostatic band 101 in the articular cavity 200 or the arthroscopy part 100 when unwinding the hemostatic block 11.

Further, according to the detailed configuration of the hemostatic unit 10, the hemostatic block 11 can be formed in a rectangular prism shape, the length of the hemostatic block 11 is easily adjusted, and the hemostatic band 11 is taken out in a flat state from the articular cavity 200 or the arthroscopy part 100 and rubbing by the hemostatic band 101 can be minimized when the hemostatic block 11 is unfolded.

Further, according to the detailed configuration of the hemostatic unit 10, the hemostatic block 11 can be formed in a hexagonal prism or rhombus prism shape, the length of the hemostatic block 11 is easily adjusted, and the hemostatic band 11 is taken out in a rolled state and rubbing by the hemostatic band 101 in the articular cavity 200 or the arthroscopy part 100 can be minimized when the hemostatic block 11 is unfolded.

Further, the hemostatic block 11 of the hemostatic unit 10 is divided into two parts and the hemostatic band 101 is taken out from between the divided hemostatic block 11, so rubbing by the hemostatic band 101 in the articular cavity 200 or the arthroscopy part 100 can be minimized.

Further, it is possible to adjust the size of the hemostatic block 11 in the articular cavity 200 using the relationship between the width of the lead line 12 and the folding-layered part 40.

Further, it is possible to stably insert the hemostatic block 11 into the articular cavity 200 through the block insertion unit 60.

Further, according to the detailed configuration of the block insertion unit 60, it is possible to stably guide the hemostatic block 11 inserted in the block guide unit 61 in position in the articular cavity 200.

Further, according to the detailed configuration of the block guide unit 61, when the block guide unit 61 is inserted into the arthroscopy part 100, rubbing by the block guide unit 61 in the arthroscopy part 100 is prevented and the hemostatic block 11 is stably taken out through the second side of the block guide unit 61. Further, when the block guide unit 61 is taken out, it is possible to prevent the guide blade 612 from rubbing the arthroscopy part 100.

Although exemplary embodiments of the present disclosure were described above with reference to the drawings, the present disclosure may be changed and modified in various ways by those skilled in the art without departing from the spirit and scope of the present disclosure described in claims.

INDUSTRIAL APPLICABILITY

The present disclosure relates to an arthroscopic bleeding control device, which can show a static absorptive and hemostatic effect against hemorrhage in an articular cavity and can stably take out a hemostatic block expanding by absorbing blood from the articular cavity without a specific tool.

What is claimed is:

1. An arthroscopic bleeding control device that shows a static absorptive and hemostatic effect against hemorrhage in an articular cavity that can be exposed by an arthroscopy part, the arthroscopic bleeding control device comprising:
   a hemostatic block configured to be inserted in the articular cavity through the arthroscopy part; and a hemostatic unit including a lead line extending from the hemostatic block to protrude outside through the arthroscopy part, wherein the hemostatic block is formed by winding or folding a hemostatic band elongated in a longitudinal direction and is then compressed in a thickness direction at least into a reference thickness for insertion into the articular cavity, so the hemostatic block can be expanded at least in the thickness direction by hemorrhage in the articular cavity, wherein, when the lead line is pulled, the hemostatic band is unwound or unfolded from the expanding hemostatic block, so the hemostatic block is taken out of the articular cavity, wherein the hemostatic block includes a spiral folded part formed by sequentially layering a first extension forming a portion of the hemostatic band, a second extension layered on the end of the first extension to cross the first extension, a third extension layered on the end of the second extension to cross the second extension and to be parallel with the first extension, a fourth extension layered on the end of the third extension to cross the third extension and the first extension and to be parallel with the second extension, and a fifth extension crossing the fourth extension and layered on the first extension, wherein the lead line extends from the first extension, and wherein the spiral folded part is compressed into the reference thickness in a layering direction of the hemostatic band.

2. The arthroscopic bleeding control device of claim 1, wherein the lead line includes:
   a first lead line; and
   a second lead line disposed to face the first lead line, and wherein the spiral folded part includes:
   a first spiral part at which the first extension extending from the first lead line, the second extension, and the third extension are sequentially layered; and
   a second spiral part at which a first extension extending from the second lead line, a second extension, and a third extension are sequentially layered.

3. The arthroscopic bleeding control device of claim 1, wherein assuming that a width of the lead line is W0 and a width of the folding-layered part is W, W=W0/2.

4. The arthroscopic bleeding control device of claim 1, further comprising a block insertion unit configured to insert the hemostatic block into the articular cavity.

5. The arthroscopic bleeding control device of claim 4, wherein the block insertion unit includes:
   a block guide unit that forms a passage for inserting the hemostatic block into the articular cavity and in which the hemostatic block is inserted; and
   a block transfer unit fitted in a first side of the block guide unit and configured to take out the hemostatic block through a second side of the block guide unit using external force.

6. The arthroscopic bleeding control device of claim 5, wherein the block guide unit includes:
   a hollow sheath tube in which the hemostatic block is inserted and in which the block transfer unit is slidably fitted at a first side; and
   a guide blade that has elasticity and closes a second side of the sheath tube, and
   wherein the guide blade opens the second side of the sheath tube by elastically deforming when the hemostatic block is slid.

* * * * *